United States Patent [19]

McFarland

[11] Patent Number: 4,772,272

[45] Date of Patent: Sep. 20, 1988

[54] NEEDLE PROTECTIVE SLEEVE

[76] Inventor: Barton C. McFarland, Mt. Sterling Rd., Rte. 2, Paris, Ky. 40361

[21] Appl. No.: 48,548

[22] Filed: May 11, 1987

[51] Int. Cl.⁴ ............................................. A61M 5/32
[52] U.S. Cl. ................................... 604/198; 604/263
[58] Field of Search ............... 604/192, 198, 263, 187, 604/232, 197

[56] References Cited

U.S. PATENT DOCUMENTS

| | | | |
|---|---|---|---|
| 2,674,246 | 4/1954 | Bower | 604/198 |
| 2,876,770 | 3/1959 | White | 604/232 |
| 2,925,083 | 2/1960 | Craig | 604/197 |
| 3,046,985 | 7/1962 | Saenz | 604/197 |
| 4,425,120 | 1/1984 | Sampson et al. | 604/198 |
| 4,631,057 | 12/1986 | Mitchell | 604/198 |
| 4,655,751 | 4/1987 | Harbaugh | 604/198 |
| 4,695,274 | 9/1987 | Fox | 604/263 X |

Primary Examiner—John D. Yasko
Attorney, Agent, or Firm—Frank C. Leach, Jr.

[57] ABSTRACT

A protective sleeve for a hypodermic needle completely overlies the needle when in a needle protection position and also overlies a needle support and at least part of a syringe to which the needle support is attached. The protective sleeve is moved from the needle protecting position to a needle injection position solely by axial movement of the protective sleeve. The protective sleeve is releasably retained in either of its positions through cooperating retaining elements on the protective sleeve and the needle support or the syringe.

20 Claims, 2 Drawing Sheets

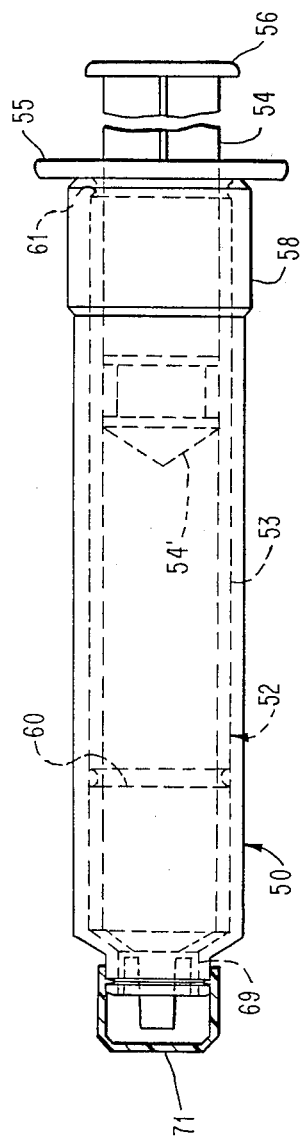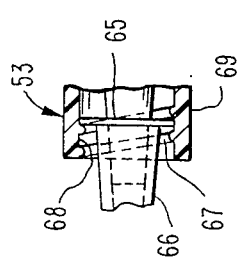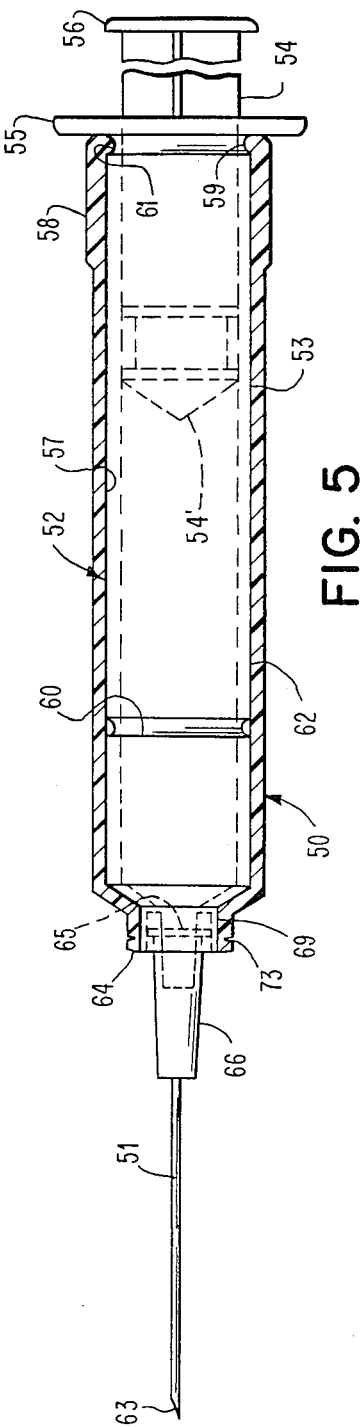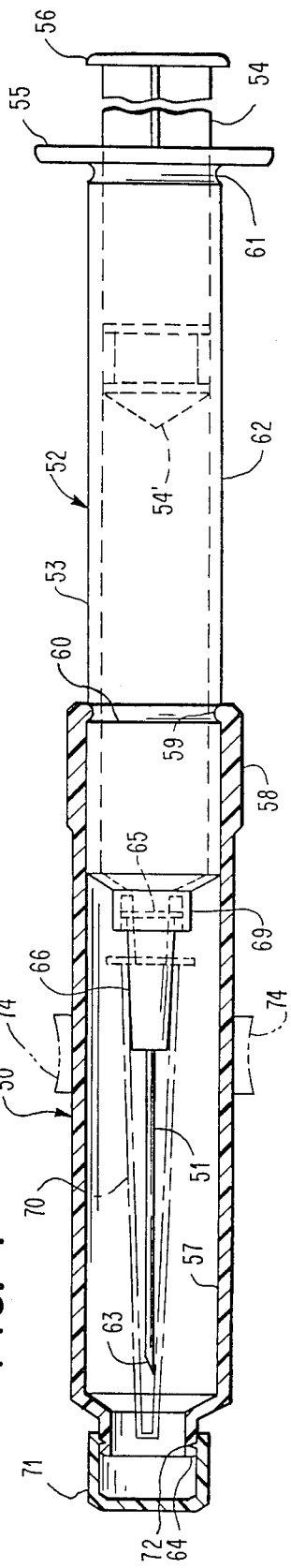

NEEDLE PROTECTIVE SLEEVE

This invention relates to a needle protective sleeve and, more particularly, to a protective sleeve for a hypodermic needle or the like in which the protective sleeve can move solely by axial movement between its needle protection position and its needle injection position.

A hollow needle such as a hypodermic needle or an intravenous needle, for example, can easily transfer an infectious disease from a patient to a medical person making an injection with the needle if the medical person has any accidental contact with the needle so that the needle breaks the skin of the medical person. With the lack of knowledge of persons having infectious diseases such as acquired immune deficiency syndrome (AIDS) and hepatitis, some patients are not aware that they have the disease and other patients may not want to tell the medical person, particularly a dentist, of the disease. Thus, a medical person, particularly a dentist, working within the mouth of a patient can accidentally engage the needle point and break the skin so as to possibly be infected from the saliva of the patient, who has the infectious disease.

Furthermore, some patients have a fear of a needle and do not wish to see it. The protective sleeve of the present invention enables the medical person to keep the needle from view of the patient until just prior to injection. With a dentist, this would permit the protective sleeve to be inserted in the patient's mouth before the needle is exposed.

Protective sleeves for hypodermic needles have been previously suggested. These include U.S. Pat. Nos. 3,040,743 to Naess, 3,314,428 to Johnson et al, 3,356,089 to Francis, 3,406,687 to Moyer, and 3,640,278 to Friedman, for example.

The aforesaid Moyer patent has a protective sheath for a relatively long hypodermic needle used for injection into a cavity of a human being. The protective sheath also functions as a guide because of the relatively long length of the needle.

The end of the protective sheath is positioned adjacent the area of the cavity into which the injection is to be made. With the end of the protective sheath held against the area of the cavity of the patient, the syringe and attached needle must be rotated 45° to permit axial movement of the needle so that its pointed end extends beyond the end of the protective sheath and into the patient. Thus, this requires the end of the protective sheath to be held by a force against the patient so that this cannot be used in many injections where such a force cannot be exerted such as in the mouth of a patient, for example.

The protective sheath of the aforesaid Moyer patent does not extend over the entire hub, which supports the needle, when the needle is in its retracted or protected position. The protective sheath also does not extend over any portion of the syringe when the needle is in its injection position. Therefore, if the needle of the aforesaid Moyer patent were shortened as would be necessary to inject within a patient's mouth, for example, and the protective sheath similarly shortened, the syringe would be exposed to the patient's saliva when used for injection in the mouth of a patient, for example.

The protective sleeve of the present invention satisfactorily solves this problem through overlying the entire needle support means and a portion of the syringe in both its needle protection position and its needle injection position. Thus, the portion of the syringe that possibly could enter the patient's mouth is protected from saliva.

Additionally, the protective sleeve of the present invention is mounted so that it is only necessary to axially move the protective sleeve with respect to the syringe to move the protective sleeve between its needle protection position and its needle injection position. This is a much simpler motion than the combined rotary and axial motion of the aforesaid Moyer patent and only requires the user to pull rearwardly on the protective sleeve when the needle is to be exposed for an injection.

Furthermore, the protective sleeve of the present invention is positively but releasably retained in either of its positions. The aforesaid Moyer patent merely relies upon engagement between a hub, which supports a needle, and a shoulder of the protective sheath to control the position of the needle rather than any retaining means therebetween. In the aforesaid Moyer patent, the protective sheath could fall from the syringe if the user were to hold the syringe vertically with the needle pointed downwardly. The protective sleeve of the present invention positively retains the protective sleeve in either of its positions so that it cannot be accidentally displaced. However, the protective sleeve can be easily released from either position by a slight axial force on the rear end of the protective sleeve.

The protective sleeve of the present invention also may be utilized with a disposable syringe. With a disposable syringe, the protective sleeve overlies the entire outer surface of the disposable syringe to prevent any contamination thereof since such syringes are not sterilized after use as are non-disposable syringes. This prevents any other person from picking up a disposable syringe and possibly being infected through a break in the skin.

An object of this invention is to provide a protective sleeve for a hypodermic needle or the like.

Another object of this invention is to provide a needle protective sleeve for use with both disposable syringes and non-disposable syringes.

A further object of this invention is to provide a protective sleeve for a hollow needle injectable into a human or an animal for supplying a liquid thereto.

Other objects of this invention will be readily perceived from the following description, claims, and drawings.

This invention relates to the combination of a hollow needle having a pointed end, means to support the needle, means connected to the needle support means to supply a liquid to the needle for injection into a human or an animal when the pointed end of the needle is inserted in a human or an animal, and a protective sleeve for disposition over the entire length of the needle when the protective sleeve is in a first position so that the pointed end of the needle is within the protective sleeve. The protective sleeve is movable solely by axial movement of the protective sleeve between its first position and a second position in which the pointed end of the needle extends beyond the protective sleeve and the protective sleeve overlies the needle support means and at least a portion of the connected means. The protective sleeve and one of the needle support means and the connected means have first cooperating means to releasably retain the protective sleeve in its first position. The protective sleeve and the one of the needle support means and the connected means have second cooperating means to releasably retain the protective sleeve in its second position.

The attached drawings illustrate preferred embodiments of the invention, in which:

FIG. 4 is an elevational view of a disposable syringe used with another embodiment of the protective sleeve of the present invention with the protective sleeve in its needle protection position and shown in section;

FIG. 5 is an elevational view of the disposable syringe and the protective sleeve of FIG. 4 with the protective sleeve in its needle injection position and shown in section;

FIG. 6 is an elevational view of the disposable syringe and protective sleeve of FIG. 4 as it is sold without a needle;

FIG. 7 is an enlarged sectional view of a needle support of the disposable syringe.

Figure 1:
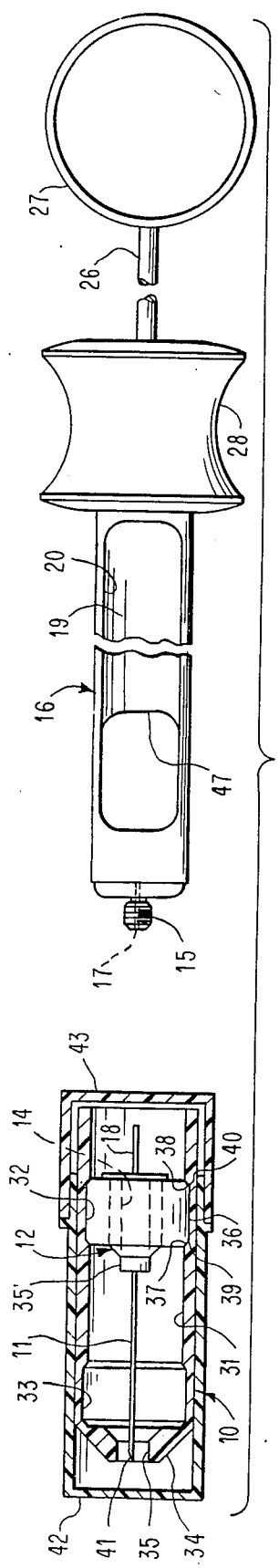
FIG. 1 is an elevational view of a non-disposable syringe and a protective sleeve of the present invention to be utilized with the syringe with the protective sleeve shown in section.

Referring to the drawings and particularly FIG. 1, there is shown a protective sleeve 10, which is preferably formed of a clear plastic such as polycarbonate, for example, for protecting a hypodermic needle 11, which is hollow. The needle 11 is supported within a hub 12 through which it extends.

The hub 12 has an interior threaded bore 14 to receive a threaded cylindrical end 15 of a non-disposable syringe 16. Thus, the needle 11 is secured to the syringe 16 when the hub 12 is attached to the cylindrical end 15 of the syringe 16. The cylindrical end 15 of the syringe 16 has a bore 17 extending therethrough to enable the needle 11 to have its rear end 18 extend into the interior of a longitudinal recess or receptacle 19 in the syringe 16 when the hub 12 is connected to the cylindrical end 15 of the syringe 16.

Figure 8:
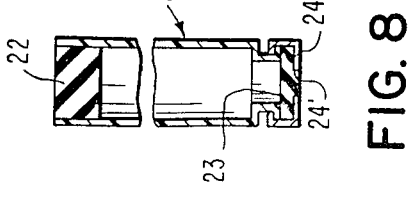
FIG. 8 is a fragmentary longitudinal sectional view of a carpule used with the syringe of FIGS. 1-3.

The recess or receptacle 19 has a longitudinal opening 20 to enable a carpule 21 (see FIG. 3) to be inserted into the recess 19. One end of the carpule 21, which is a substantially cylindrical shaped hollow element of clear plastic, is closed by a movable rubber plug 22 (see FIG. 8) and its other end has a reduced portion closed by a rubber plug 23, which is supported by a metal cap 24 having an opening 24', so that the rear end 18 (see FIG. 1) of the needle 11 extends through the opening 24' (see FIG. 8) in the metal cap 24 and the rubber plug 23 into the interior of the carpule 21 to receive liquid when there is to be an injection.

The rubber plug 23 of the carpule 21 is pushed into the rear end 18 (see FIG. 1) of the needle 11 when a hook 25 (see FIG. 3) on one end of a plunger 26 is advanced into engagement with the rubber plug 22 (see FIG. 8) of the carpule 21. The plunger 26 (see FIG. 3), which is a rod having a handle 27 on its other end, is slidably supported by an end 28 of the syringe 16. Withdrawal of the plunger 26 is limited by a flange 29 on the end of the plunger 26 having the hook 25 engaging a spring 30 within the end 28 of the syringe 16.

Figure 3:
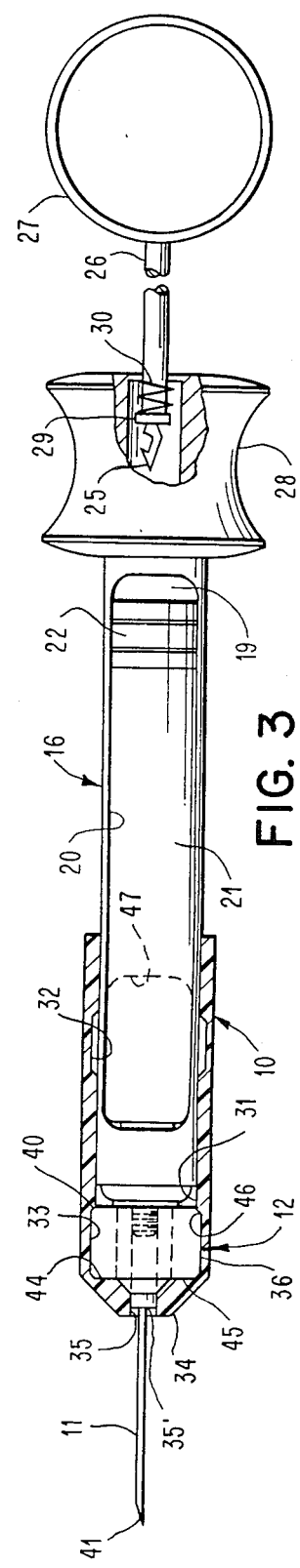
FIG. 3 is an elevational view of the syringe and the protective sleeve of FIG. 2 having a carpule in the syringe with the protective sleeve disposed in its needle injection position and shown in section.

The protective sleeve 10 (see FIG. 1) is a substantially hollow cylinder having its inner surface 31 of a substantially constant diameter throughout its length except for a first annular groove 32 and a second annular groove 33. The protective sleeve 10 has a conical shaped end 34 adjacent the second annular groove 33 and providing a relatively large passage 35 in comparison with the size of the needle 11 through which the needle 11 can be advanced and retracted. The relatively large passage 35 accommodates an end 35' of the hub 12 when the protective sleeve 10 is in its needle injection position as shown in FIG. 3.

When the protective sleeve 10 is in the position of FIG. 1, the first annular groove 32 grips an outer surface 36 of the hub 12 so that angled end surfaces 37 and 38 of the first annular groove 32 engage angled end surfaces 39 and 40 of the hub 12. This releasably retains the protective sleeve 10 in the position of FIG. 1 in which the needle 11 has its pointed end 41, which is to be inserted into the patient, protected by the protective sleeve 10.

The protective sleeve 10 and the needle 11 can be sold as a unit in a package having overlapping end covers 42 and 43 cooperating with each other to encompass the protective sleeve 10 and the needle 11. This package of the overlapping end covers 42 and 43 is shown in FIG. 1.

Figure 2:
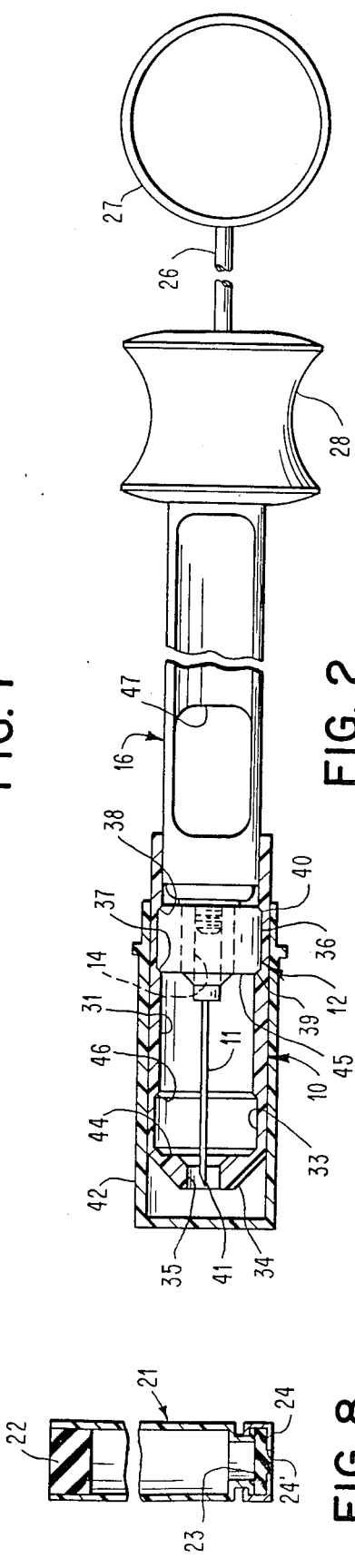
FIG. 2 is an elevational view of the syringe of FIG. 1 having the needle of FIG. 1 attached thereto with the protective sleeve in its needle protection position and the protective sleeve shown in section.

When the needle 11 is to be attached to the syringe 16, the end cover 43 is removed, and the cylindrical end 15 of the syringe 16 threaded into the bore 14 of the hub 12 as shown in FIG. 2. Next, one of the carpules 21 (see FIG. 3) is inserted through the longitudinal opening 20 (see FIG. 1) into the recess or receptacle 19 of the syringe 16. Then, the end cover 42 is removed from the protective sleeve 10.

The needle 11 may now be positioned close to the area of the patient in which the pointed end 41 of the needle 11 is to be inserted. Then, the protective sleeve 10 is moved solely by an axial pull on the rear of the protective sleeve 10 from the position of FIG. 2 to the position of FIG. 3 in which the needle 11 fully extends beyond the conical shaped end 34 of the protective sleeve 10. The protective sleeve 10 is moved through releasing the hub 12 from the first annular groove 32 by pulling axially in a rearward direction (to the right in FIG. 2) on the protective sleeve 10. The angled end surface 37 of the first annular groove 32 in the inner surface 31 of the protective sleeve 10 easily slides up the angled end surface 39 of the hub 12 as the protective sleeve 10 is moved to the right in FIG. 2. With the protective sleeve 10 being moved to the right, a flat surface 44 of the conical shaped end 34 of the protective sleeve 10 abuts a flat surface 45 of the hub 12. At this time, the hub 12 is disposed within the second annular groove 33, as shown in FIG. 3, to releasably retain the hub 12 in its needle injection position.

Then, by the user pushing on the plunger 26 towards the end 28 of the syringe 16 (to the left in FIG. 3) to advance the rubber plug 22 within the carpule 21, the liquid in the carpule 21 is passed through the needle 11 to the patient in which the pointed end 41 of the needle 11 has been inserted. When the injection of the liquid is completed and the pointed end 41 of the needle 11 withdrawn from the patient, the protective sleeve 10 is pushed by the user to the left in FIG. 3 to return the protective sleeve 10 to the position of FIG. 2. The second annular groove 33 in the inner surface 31 of the protective sleeve 10 has an angled end surface 46 cooperating with the angled end surface 40 of the hub 12 to enable the protective sleeve 10 to be released from its releasable retention by the hub 12.

Thus, the protective sleeve 10 overlies the hub 12 in either its needle protection position or its needle injection position. The protective sleeve 10 also overlies a portion of the syringe 16 in its needle protection position as shown in FIG. 2 and a substantially greater portion of the syringe 16 in its needle injection position as shown in FIG. 3.

When the medical person is finished using the needle 11 for a specific patient, the carpule 21 is withdrawn from engagement with the rear end 18 (see FIG. 1) of the needle 11 by the hook 25 being engaged with the rubber plug 22 (see FIG. 8) of the carpule 21. The carpule 21 may be pushed from the recess 19 (see FIG. 1) through the user pushing a finger through an opening 47 in the syringe 16 diametrically opposite to the longitudinal opening 20.

Then, it is necessary to disconnect the hub 12 from the cylindrical end 15 of the syringe 16. First, the protective sleeve 10 should be in its needle protection position of FIG. 2. If desired, the end cover 42 (see FIG. 1) also can be placed thereover. After disconnecting the hub 12 from the cylindrical end 15 of the syringe 16, the end cover 43 may be replaced over the end cover 42 to form a complete package again for disposal purposes, if desired. The end cover 43 prevents the user from engaging the rear end 18 of the needle 11 although it cannot be contaminated.

Referring to FIG. 4, there is shown a protective sleeve 50 for use with a hollow needle 51 releasably attached to a disposable syringe 52. The disposable syringe 52 includes a hollow barrel 53, which is formed of a clear plastic such as polycarbonate, for example, storing a liquid to be injected into a patient through the needle 51.

A plunger 54, which has a rubber plug 54' at its end for sliding sealing engagement with the hollow barrel 53, is slidably disposed within the hollow barrel 53 to close the open end of the hollow barrel 53 and retain the liquid therein. The plunger 54 extends beyond an end flange 55 of the hollow barrel 53. The plunger 54 has a flange 56 on its end to limit the maximum advancement of the plunger 54 within the barrel 53 by the flange 56 engaging the end flange 55 on the barrel 53.

The protective sleeve 50 is substantially a hollow cylinder having its inner surface 57 on a substantially constant diameter throughout its length. The protective sleeve 50 has a rear end 58, which has serrations on its outer surface, with a larger outer diameter than the hollow cylinder. The rear end 58 has an annular projection 59 extending inwardly for cooperation with either an annular groove 60 or an annular groove 61 in an outer surface 62 of the hollow barrel 53.

When the annular projection 59 is disposed in the annular groove 60 as shown in FIG. 4, the protective sleeve 50 is in its needle protection position. The needle 51 has its pointed end 63 substantially spaced from a reduced end 64 of the protective sleeve 50.

The needle 51 is attached to the disposable syringe 52 through a rear flange 65 of a collar 66, which has the needle 51 fixed therein, being positioned within a curved track 67 (see FIG. 7) in an inner surface 68 of a reduced hollow cylindrical portion 69 at one end of the hollow barrel 53 (see FIG. 4) of the disposable syringe 52 and then rotated relative thereto. This locks the needle 51 to the hollow barrel 53 of the disposable syringe 52 for support.

Since the needle 51 is purchased separately from the disposable syringe 52, a protective needle cover 70 (shown in phantom) fits over the needle 51. The cover 70 has a tight fit with the outer surface of the collar 66 to which the needle 51 is fixed. The protective sleeve 50 also has a cap 71 mounted on the reduced end 64 and retained thereon through an annular pointed projection 72 on the cap 71 extending into an annular V-shaped groove 73 (see FIG. 5) in the reduced end 64 of the protective sleeve 50.

When the needle 51 is to have the pointed end 63 inserted into the patient, the cap 71 (see FIG. 4) and the needle cover 70 are removed. Then, the protective sleeve 50 is moved solely in an axial direction with the annular projection 59 being pulled out of the annular groove 60 so that the protective sleeve 50 is moved from the position of FIG. 4 to the position of FIG. 5 in which the needle 51 is completely exposed so that the protective sleeve 50 is in its needle injection position. The protective sleeve 50 is releasably retained in this position by the annular projection 59 being disposed in the annular groove 61 in the outer surface 62 of the hollow barrel 53 of the disposable syringe 52.

When the protective sleeve 50 is in its needle protection position of FIG. 4, it overlies a portion of the outer hollow barrel 53 of the disposable syringe 52. When the protective sleeve 50 is in its needle injection position of FIG. 5, the protective sleeve 50 completely overlies the hollow barrel 53 of the disposable syringe 52.

After use of the needle 51 is completed in which the rubber plug 54' of the plunger 54 is advanced towards the portion 69 of the hollow barrel 52 to supply liquid therefrom, the protective sleeve 50 is moved axially from the position of FIG. 5 to the position of FIG. 4 in which the needle 51 has the pointed end 63 within the protective sleeve 50. Then, if desired, the cap 71 can be mounted on the reduced end 64 of the protective sleeve 50 although such is not necessary because of the pointed end 63 of the needle 51 being spaced from the reduced end 64 of the protective sleeve 50. Then, the disposable syringe 52 and the protective sleeve 50 are discarded.

If desired, the protective sleeve 50 may have a pair of diametrically disposed finger grips (shown in phantom at 74 in FIG. 4) formed integral therewith. Each of the grips 74 would extend for about 10° around the circumference of the protective sleeve 50.

While the protective sleeve of this invention has been shown and described as being used with a hypodermic needle supported by a syringe, the protective sleeve also could be used with a hollow needle for intravenous injection, for example.

An advantage of this invention is that it prevents contamination of a hypodermic needle or the like injected into a human or an animal. Another advantage of this invention is that it enables a medical person to prevent a patient from seeing the needle by not exposing the needle until it is disposed adjacent the area of the patient in which it is to be inserted. A further advantage of this invention is that it provides sterile protection to the portion of the syringe that would enter a patient's mouth and be contaminated without the protective sleeve.

For purposes of exemplification, preferred embodiments of the invention have been shown and described according to the best present understanding thereof.

However, it will be apparent that changes and modifications in the arrangement and construction of the parts thereof may be resorted to without departing from the spirit and scope of the invention.

I claim:
1. In combination:
a hollow needle having a pointed end;
means to support said needle;
means connected to said needle support means to supply a liquid to said needle for injection into a human or an animal when said pointed end of said needle is inserted in a human or an animal;
a protective sleeve for disposition over the entire length of said needle when said protective sleeve is in a first position so that said pointed end of said needle is within said protective sleeve;
said protective sleeve being movable solely by axial movement of said protective sleeve between its first position and a second position in which said pointed end of said needle extends beyond said protective sleeve and said protective sleeve overlies said needle support means and at least a portion of said connected means;
said protective sleeve and one of said needle support means and said connected means having first cooperating means to releasably retain said protective sleeve in its first position;
said protective sleeve and said one of said needle support means and said connected means having second cooperating means to releasably retain said protective sleeve in its second position;
said protective sleeve in its second position exposing substantially the entire length of said needle including said pointed end;
said protective sleeve is a substantially hollow cylinder having an inner surface and its opposite ends open;
said connected means including:
a barrel having a recess to receive liquid containing means containing a liquid for injection;
and plunger means for forcing the liquid from the liquid containing means in said recess into said needle for injection through said pointed end of said needle;
said needle support means including a hub connected to said barrel and having said needle attached thereto and extending therethrough for penetration into the liquid containing means in said recess;
and said protective sleeve extending over said hub and at least a portion of said barrel in each of its first and second positions.

2. The combination according to claim 1 in which:
said first cooperating means includes at least a portion of said hub and first means in said inner surface of said substantially hollow cylinder of said protective sleeve to grip said portion of said hub to releasably retain said protective sleeve in its first position;
and said second cooperating means includes said portion of said hub and second means in said inner surface of said substantially hollow cylinder of said protective sleeve to grip said portion of said hub to releasably retain said protective sleeve in its second position.

3. The combination according to claim 2 in which said hub is releasably connected to said barrel.

4. The combination according to claim 2 in which said protective sleeve has a substantially tight fit with said portion of said barrel over which said protective sleeve extends in each of its first and second postions.

5. The combination according to claim 1 in which:
said hub is releasably connected to said barrel;
and said hub is said one of said needle support means and said connected means.

6. The combination according to claim 1 in which said protective sleeve has a substantially tight fit with said portion of said barrel over which said protective sleeve extends in each of its first and second positions.

7. The combination according to claim 1 in which said inner surface of said substantially hollow cylinder of said protective sleeve has a constant diameter except at its end through which said needle extends when said protective sleeve is in its second position and at said first and second cooperating means of said protective sleeve.

8. The combination according to claim 2 in which said inner surface of said substantially hollow cylinder of said protective sleeve has a constant diameter except at its end through which said needle extends when said protective sleeve is in its second position and at said first and second cooperating means of said protective sleeve.

9. The combination according to claim 1 in which said protective sleeve has a substantially tight fit with said hub in each of its first and second positions.

10. In combination:
a hollow needle having a pointed end for insertion into a human or an animal;
a hub having said needle attached thereto for support thereby and extending therethrough so that said needle has its rear end extending beyond said hub;
means releasably connected to said hub and having said rear end of said needle extend thereinto to enable said needle to have liquid flow therethrough when said pointed end of said needle is inserted in a human or an animal;
a protective sleeve for disposition over the entire length of said needle when said protective sleeve is in a first position so that said pointed end of said needle is within said protective sleeve;
said protective sleeve being movable solely by axial movement of said protective sleeve between its first position and a second position in which said pointed end of said needle extends beyond said protective sleeve and said protective sleeve overlies said hub and at least a portion of said releasably connected means;
said protective sleeve and said hub having first cooperating means to releasably retain said protective sleeve in its first position solely by axial movement of said protective sleeve to its first position;
said protective sleeve and said hub having second cooperating means to releasably retain said protective sleeve in its second position solely by axial movement of said protective sleeve to its second position;
said protective sleeve in its second position exposing substantially the entire length of said needle including said pointed end;
and said protective sleeve is a substantially hollow cylinder having an inner surface and its opposite ends open.

11. The combination according to claim 10 in which:
said releasably connected means includes:
a barrel having a recess to receive liquid containing means containing a liquid for injection;
and plunger means for forcing the liquid from the liquid containing means in said recess into said needle for injection through said pointed end of said needle;

said hub is releasably connected to said barrel;

said rear end of said needle penetrates into the liquid containing means in said recess in said barrel;

and said protective sleeve extends over said hub and at least a portion of said barrel in each of its first and second positions.

12. The combination according to claim 11 in which:

said first cooperating means includes at least a portion of said hub and first means in said inner surface of said substantially hollow cylinder of said protective sleeve to grip said portion of said hub to releasably retain said protective sleeve in its first position;

and said second cooperating means includes said portion of said hub and second means in said inner surface of said substantially hollow cylinder of said protective sleeve to grip said portion of said hub to releasably retain said protective sleeve in its second position.

13. The combination according to claim 12 in which said protective sleeve has a substantially tight fit with said portion of said barrel over which said protective sleeve extends in each of its first and second positions.

14. The combination according to claim 12 including:

cover means for said hub and said hollow needle when said releasably connected means is not connected to said hub and said protective sleeve is in its first position;

and said cover means including:

a first end cover overlying a portion of said substantially hollow cylinder of said protective sleeve including one of said opposite ends of said substantially hollow cylinder;

and a second end cover overlying the remainder of said substantially hollow cylinder of said protective sleeve including the other of said opposite ends of said substantially hollow cylinder of said protective sleeve.

15. The combination according to claim 10 in which:

said first cooperating means includes at least a portion of said hub and first means in said inner surface of said substantially hollow cylinder of said protective sleeve to grip said portion of said hub to releasably retain said protective sleeve in its first position;

and said second cooperating means includes said portion of said hub and second means in said inner surface of said substantially hollow cylinder of said protective sleeve to grip said portion of said hub to releasably retain said protective sleeve in its second position.

16. The combination according to claim 15 including:

cover means for said hub and said hollow needle when said releasably connected means is not connected to said hub and said protective sleeve is in its first position;

and said cover means including:

a first end cover overlying a portion of said substantially hollow cylinder of said protective sleeve including one of said opposite ends of said substantially hollow cylinder;

and a second end cover overlying the remainder of said substantially hollow cylinder of said protective sleeve including the other of said opposite ends of said substantially hollow cylinder of said protective sleeve.

17. The combination according to claim 10 in which said inner surface of said substantially hollow cylinder of said protective sleeve has a constant diameter except at its end through which said needle extends when said protective sleeve is in its second position and at said first and second cooperating means of said protective sleeve.

18. The combination according to claim 12 in which said inner surface of said substantially hollow cylinder of said protective sleeve has a constant diameter except at its end through which said needle extends when said protective sleeve is in its second position and at said first and second cooperating means of said protective sleeve.

19. The combination according to claim 15 in which said inner surface of said substantially hollow cylinder of said protective sleeve has a constant diameter except at its end through which said needle extends when said protective sleeve is in its second position and at said first and second cooperating means of said protective sleeve.

20. The combination according to claim 21 in which said inner surface of said substantially hollow cylinder of said protective sleeve has said first and second cooperating means of said protective sleeve on its portion having the constant diameter.

* * * * *

UNITED STATES PATENT AND TRADEMARK OFFICE
CERTIFICATE OF CORRECTION

PATENT NO. : 4,772,272

DATED : September 20, 1988

INVENTOR(S) : Barton C. McFarland

It is certified that error appears in the above-identified patent and that said Letters Patent is hereby corrected as shown below:

Column 10, line 42, "21" should read -- 1 --.

Signed and Sealed this

Thirty-first Day of January, 1989

*Attest:*

DONALD J. QUIGG

*Attesting Officer*  *Commissioner of Patents and Trademarks*